(12) United States Patent
An et al.

(10) Patent No.: US 10,660,602 B2
(45) Date of Patent: May 26, 2020

(54) ENERGY EFFICIENT HEART SOUND DATA COLLECTION

(71) Applicant: Cardiac Pacemakers, Inc., St. Paul, MN (US)

(72) Inventors: Qi An, Blaine, MN (US); Pramodsingh Hirasingh Thakur, Woodbury, MN (US); Keith R. Maile, New Brighton, MN (US); Bin Mi, Plymouth, MN (US); John D. Hatlestad, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 155 days.

(21) Appl. No.: 15/634,677

(22) Filed: Jun. 27, 2017

(65) Prior Publication Data
US 2018/0008228 A1    Jan. 11, 2018

Related U.S. Application Data

(60) Provisional application No. 62/358,978, filed on Jul. 6, 2016.

(51) Int. Cl.
| | |
|---|---|
| *A61B 7/04* | (2006.01) |
| *A61N 1/365* | (2006.01) |
| *A61B 5/00* | (2006.01) |
| *A61B 7/00* | (2006.01) |
| *A61B 5/024* | (2006.01) |

(Continued)

(52) U.S. Cl.
CPC ............ *A61B 7/04* (2013.01); *A61B 5/0004* (2013.01); *A61B 5/02405* (2013.01);
(Continued)

(58) Field of Classification Search
CPC ... A61B 7/04; A61B 7/045; A61B 2562/0204; A61B 2560/0209; A61B 5/7285; A61B 5/02438
See application file for complete search history.

(56) References Cited

U.S. PATENT DOCUMENTS 5,010,889 A * 4/1991 Bredesen ................. A61B 7/04
381/67
7,115,096 B2  10/2006 Siejko et al.
(Continued)

FOREIGN PATENT DOCUMENTS

WO    WO-2018009377 A1    1/2018

OTHER PUBLICATIONS

"International Application Serial No. PCT/US2017/039504, International Search Report on Patentability dated Jan. 17, 2019", 7 pgs.
(Continued)

*Primary Examiner* — Alyssa M Alter
(74) *Attorney, Agent, or Firm* — Schwegman Lundberg & Woessner, P.A.

(57) ABSTRACT

This document discusses, among other things, apparatus, systems, or methods to efficiently collect heart sound data, including detecting first heart sound information of a heart of a patient using a heart sound sensor in a first, low-power operational mode, and detecting second heart sound information of the heart using the heart sound sensor in a separate second, high-power operational mode. The operational mode of the heart sound sensor can be controlled using physiologic information from the patient, including heart sound information, information about a heart rate of the patient, or other physiologic information from the patient that indicates worsening heart failure.

20 Claims, 3 Drawing Sheets

(51) Int. Cl.
*A61B 5/11* (2006.01)
*A61B 5/08* (2006.01)
*A61N 1/362* (2006.01)
*A61B 5/0402* (2006.01)
*A61B 5/053* (2006.01)

(52) U.S. Cl.
CPC ........ *A61B 5/02438* (2013.01); *A61B 5/4842* (2013.01); *A61B 5/686* (2013.01); *A61B 5/7282* (2013.01); *A61B 5/7285* (2013.01); *A61B 7/00* (2013.01); *A61N 1/36578* (2013.01); *A61B 5/024* (2013.01); *A61B 5/0402* (2013.01); *A61B 5/0531* (2013.01); *A61B 5/0816* (2013.01); *A61B 5/1118* (2013.01); *A61B 5/7292* (2013.01); *A61B 2560/0209* (2013.01); *A61B 2562/0204* (2013.01); *A61N 1/3627* (2013.01)

(56) References Cited

U.S. PATENT DOCUMENTS

| | | |
|---|---|---|
| 2004/0127792 A1 | 7/2004 | Siejko et al. |
| 2006/0161070 A1 | 7/2006 | Siejko et al. |
| 2008/0119749 A1 | 5/2008 | Haro et al. |
| 2008/0125820 A1 | 5/2008 | Stahmann et al. |
| 2017/0071551 A1* | 3/2017 | Jain ................. A61B 5/0006 |

OTHER PUBLICATIONS

"International Application Serial No. PCT/US2017/039504, International Search Report dated Oct. 5, 2017", 5 pgs.

"International Application Serial No. PCT/US2017/039504, Written Opinion dated Oct. 5, 2017", 7 pgs.

* cited by examiner

ENERGY EFFICIENT HEART SOUND DATA COLLECTION

CLAIM OF PRIORITY

This application claims the benefit of priority under 35 U.S.C. § 119(e) of U.S. Provisional Patent Application Ser. No. 62/358,978, filed on Jul. 6, 2016, which is herein incorporated by reference in its entirety.

TECHNICAL FIELD

This document relates generally to medical devices, and more particularly, but not by way of limitation, to system, devices, and methods for energy efficient heart sound data collection.

BACKGROUND

Implantable medical devices, such as cardiac rhythm management (CRM) devices, can be used to monitor, detect, or treat various cardiac conditions that can result in a reduced ability of a heart to sufficiently deliver blood to a body. In some cases, heart conditions may lead to rapid, irregular, or inefficient heart contractions, etc. To alleviate one or more of these conditions, various medical devices can be implanted in a patient's body to monitor heart activity or to provide electrical stimulation to optimize or control contractions of the heart.

Traditional cardiac rhythm management (CRM) devices, such as pacemakers or defibrillators, include subcutaneous devices implanted in a chest of a patient, having one or more leads to position one or more electrodes or other sensors at various locations in the heart, such as in one or more of the atria or ventricles. The CRM device can include one or more electrodes or other sensors (e.g., a pressure sensor, an accelerometer, a gyroscope, a microphone, etc.) powered by a power source in the CRM device having a limited capacity. The one or more electrodes or other sensors of the leads, the CRM device, or a combination thereof, can be configured detect physiologic information from, or provide one or more therapies or stimulation to, the patient.

Leadless devices, such as implantable cardiac monitors, leadless cardiac pacemakers (LCP), insertable cardiac monitors (ICM), etc., and external devices, such as wearable remote patient monitors, etc., have developed that can detect physiologic information from, and in certain examples, provide one or more therapies or stimulation to the heart, without traditional lead or implantable CRM device complications. Such leadless and wearable devices are typically small, self-contained devices (e.g., smaller than traditional implantable CRM devices), in certain examples, having even more limited power and processing capabilities than a traditional CRM device.

SUMMARY

This document discusses, among other things, apparatus, systems, or methods to efficiently collect heart sound data, including detecting first heart sound information of a heart of a patient using a heart sound sensor in a first, low-power operational mode, and detecting second heart sound information of the heart using the heart sound sensor in a separate second, high-power operational mode. The operational mode of the heart sound sensor can be controlled using physiologic information from the patient, including heart sound information, information about a heart rate of the patient, or other physiologic information from the patient that indicates worsening heart failure.

An example system can include a heart sound sensor configured to detect first heart sound information of a heart of a patient in a first, low-power operational mode and second heart sound information of the heart in a separate second, high-power operational mode, and a heart sound control circuit configured to receive physiologic information from the patient and control the operational mode of the heart sound sensor using the received physiologic information.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
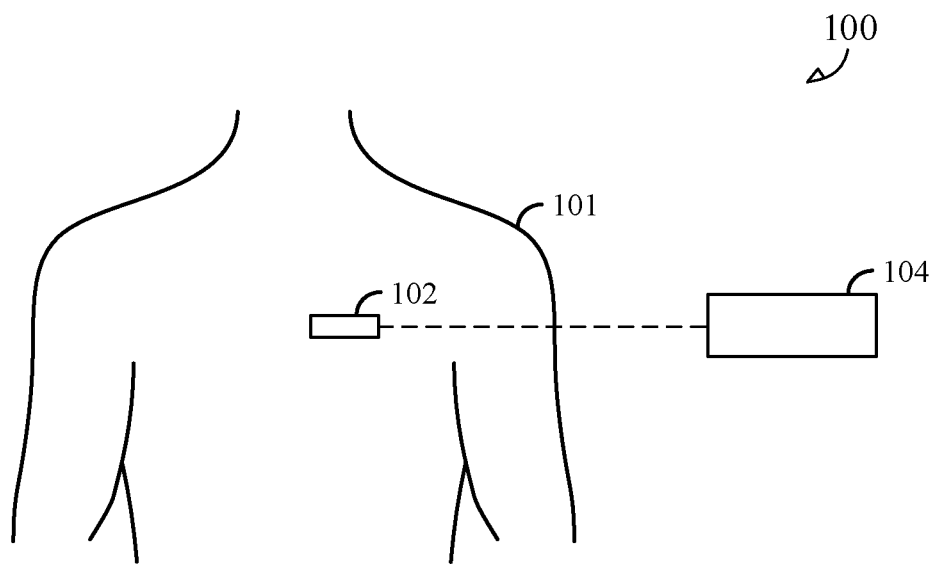
FIGS. 1-2 illustrate example systems and apparatus, including a heart sound sensor and a heart sound control circuit.

Heart sounds are recurring mechanical signals associated with cardiac vibrations from blood flow through the heart with each cardiac cycle, and can be separated and classified according to activity associated with the vibrations and blood flow. Heart sounds include four major sounds: the first through the fourth heart sounds. The first heart sound (S1) is the vibrational sound made by the heart during closure of the atrioventricular (AV) valves. The second heart sound (S2) is a cardiac vibration by the aortic and pulmonary valves at the beginning of diastole. The third and fourth heart sounds (S3, S4) are cardiac vibrations related to filling pressures of the left ventricle during diastole.

Various physiologic conditions can be detected using heart sounds, including, for example, acute physiologic events, such as one or more abnormal cardiac rhythms (e.g., atrial fibrillation, atrial flutter, cardiac mechanical dyssynchrony, etc.), as well as more chronic physiologic events, such as heart failure, ischemia, etc.

The present inventors have recognized, among other things, that heart sounds, and specifically the third heart sound (S3) (e.g., absolute or relative measurements of amplitude, timing, energy, morphology, etc.), are the most prominent physiologic sensor information to predict or stratify the onset or risk of heart failure decompensation, as both a risk assessment indicator (e.g., using absolute levels of S3), and in a prediction model (e.g., using relative changes of S3). As the size of medical devices decreases, and as chronic, remote, ambulatory, long-term monitoring of heart sound activity becomes more prevalent, it can be advantageous to more efficiently detect and store heart sound information, without sacrificing data necessary for physiologically beneficial heart sound detection, for example, to enable long term, chronic, remote monitoring of a patient without regular connectivity to a remote monitoring service or device, or to increase the amount of physiologic data storage or processing capability of medical devices. The systems, devices, and methods disclosed herein can enable more efficient patient monitoring of heart sound information for any type of medical device, including implantable, subcutaneous, wearable, or external devices.

For example, acute, high-resolution measurements of heart sounds, such as S3, may not be feasible at all times in all devices, including insertable cardiac monitors (ICM) or leadless cardiac pacemakers (LCP), due to the power consumption or processing requirements of existing detection algorithms. Existing low/ultralow-noise heart sound detection algorithms require an accelerometer having a high-power mode (e.g., low-noise, high sampling rate) for heart sound detection, which requires substantially more current than, for example, detecting activity with an accelerometer with a normal-operation mode (e.g., more than double, 5×, 7×, or more, etc.). Whereas an accelerometer may require a first amount of current for activity monitoring (e.g., 1-2 uA), such activity-monitoring mode may be insufficient to detect necessary heart sound information from the patient, and existing low/ultralow-noise heart sound detection algorithms may require a second, much higher amount of current (e.g., 10-15 uA).

Further, in certain examples, the power required to write the detected heart sound information to flash memory for extended storage may dominate power usage of a device at the time the heart sound information is stored. Accordingly, in certain devices (e.g., an ICM), switching from 10 flash writings per day (e.g., acute, high-power mode) to 1 flash writing per day (e.g., chronic, low-power mode) can represent an extension of 2 months or more of device longevity. In other examples, to save power, heart sound data (e.g., inter-day data) may be stored in non-flash memory for processing, then intermittently transferred to flash memory (e.g., several times per day, once per day, once every several days, etc.).

The information being stored may also be optimized to improve device efficiency. For example, heart sound information, such as that to be stored in memory, can include an ensemble average of the particular heart sound over a specified time period (e.g., 30 seconds, one minute, etc.) or number of physiologic cycles, such as that disclosed in the commonly assigned Siejko et al. U.S. Pat. No. 7,115,096 entitled "THIRD HEART SOUND ACTIVITY INDEX FOR HEART FAILURE MONITORING," which is hereby incorporated by reference in its entirety, including its disclosure of ensemble averaging an acoustic signal. Similar to the number of flash writings per day, a decrease from 72 ensemble average sessions per day (e.g., acute, high-power mode) to one ensemble average per day (e.g., chronic, low-power mode) may represent an increase in device longevity by two months or more due to accelerometer power decreases alone. Any decrease from an existing number of ensemble average sessions per day (e.g., from 72 to 40, 30, 20, etc.) may represent a decrease in device power consumption and a corresponding increase in device longevity.

To detect specific heart sounds, a physiologic cycle (e.g., a cardiac cycle) can be gated into specific detection windows corresponding to each heart sound. The windows generally have a predefined duration and are triggered by some physiologic information. For example, as the first heart sound (S1) window can be triggered using a feature of the QRS complex (e.g., the R-wave), the second heart sound (S2) window can be triggered using the end of the T-wave, and the fourth heart sound (S4) window, if present, using the P-wave. The third heart sound (S3) window, however, is typically triggered using a time period in relation to S2 or the S2 window. Accordingly, to detect S3, S2 is first detected, or the S2 window is calculated. Such detection of S3 is commonly referred to as "S2 tracking mode". The present inventors have recognized, among other things, that, to save power (e.g., in chronic, low-power mode), the S3 window can be estimated using other physiologic information, such as a heart rate of the patient, etc.

To ensure that a specific heart sound occurs in a specific heart sound window, the length of the windows can be extended. However, the power required by the accelerometer to detect heart sounds in each respective window, as well as the amount of data to be processed, is proportional to the length of the window. Accordingly, to save power (e.g., in chronic, low-power mode), the length of one or more detection windows can be reduced. For example, reducing the S3 window (e.g., with a corresponding adjustment of S2-S3 delay) can result in a substantial power savings for the accelerometer, while retaining detection capabilities of underlying physiologic conditions, such as using S3 amplitude, power, timing, or morphology to detect an indication of worsening heart failure (HF) or HF status of the patient, etc. In other examples, the S4 window can be reduced when detecting atrial fibrillation (AF), or one or more of the S1 or S2 windows can be reduced, etc.

Further, the sampling frequency of the accelerometer can be reduced (e.g., from 200 Hz in acute, high-power mode, to 100 Hz or lower in chronic, low-power mode, etc.). In an example, using Nyquist's law, measurements as low as 50 Hz (and in certain examples, lower) can be made in the chronic, low-power mode, depending on frequency of desired heart sound data. In other examples, other low power modes of the accelerometer can be used (e.g., wake-up mode, normal mode, or low-noise mode instead of ultra-low-noise mode), reducing power consumption of the accelerometer and the amount of data to be processed or stored, while still detecting clinically useful heart sound information.

In other examples, detection of heart sound information using the accelerometer can be gated or triggered using various physiologic information, such as to avoid extended use of high-current sensor data (e.g., the ultra-low-noise mode of the accelerometer, etc.). For example, detection of one or more heart sounds (e.g., S3) can be first made in a low-power mode of the accelerometer (e.g., wake-up mode, normal mode, low-noise mode, etc.) which, if a threshold condition is reached, can trigger subsequent detection of the one or more heart sounds (e.g., S3) in a higher-power mode (e.g., ultra-low-noise mode, etc.) of the accelerometer. For example, S3 detection (e.g., S3 amplitude, the relative change in S3 power or amplitude (more reliable in chronic, low-power mode), etc.) in low-power mode can show a high probability of worsening heart failure, which, in certain examples, can then be used to trigger an acute, high-power mode of the accelerometer, or can be used alone as an indication of worsening heart failure.

In an example, detection of one heart sound (e.g., S1, S2, S3, etc.) exceeding a threshold condition in a low or high-power mode can trigger detection of another heart sound (e.g., S3) in a low or high-power mode. Further, the threshold condition trigger from a low-power mode to a high-power mode can be used as a second trigger after an initial first trigger (e.g., detection of S1 in a low-power mode exceeding a threshold can trigger detection of S2 in a low-power mode, and subsequent detection of S2 in a low-power mode exceeding a threshold can trigger detection of S2 in a higher-power mode, etc.).

In other examples, other physiologic information can be used as a trigger condition for heart sound detection, or in combination with such heart sound detection, such as respiration (e.g., rate, phase, volume, etc.), activity (e.g., active or inactive, during or after a period of activity, etc.), patient posture (e.g., while the patient is in a specific position, such as laying down, sitting, standing upright, walking, etc.), heart rate (e.g., when the heart rate increases or decreases, is above or below a specific threshold, nighttime heart rate, daytime heart rate, heart rate variability, etc.), impedance, or any combination or permutation of the above (e.g., heart rate during activity, respiration rate during activity or in a specific posture, etc.). Once a threshold condition of one or more of these physiologic information is reached, low or high-power heart sound detection can be triggered, such as described above. Further, in certain examples, physiologic information can be used to gate heart sound detection (e.g., heart sound detection can be suspended when the patient is active, etc.).

In other examples, S2 tracking mode or one or more other power saving features disclosed herein can be selectively enabled or disabled in various combinations or permutations, effectively creating a number of different power-saving modes. Further, heart sound detection in the acute, high-power operational mode can be limited, such that, if data collection fails a number of times, detection can be postponed until a later time (e.g., when a patient is not active, a different time of day, etc.).

FIG. 1 illustrates an example system 100 including an insertable cardiac monitor (ICM) 102 configured to sense physiologic information from a patient 101. The ICM 102 can be implanted or positioned subcutaneously within the patient 101, and in certain examples, can be configured to provide one or more stimulations or therapies to the patient 101.

In an example, the system 100 can include an external device 104 (e.g., an external programmer, etc.) configured to be communicatively coupled to the ICM 102 using a telemetry circuit and a wireless communication protocol. In other examples, the system can include one or more other implantable (e.g., an implantable pacemaker, defibrillator, leadless cardiac pacer (LCP), etc.) or external (e.g., wearable, etc.) devices, coupled to, or instead of, the ICM 102, with one or more of the ICM 102 or other implantable or external devices configured to be coupled to at least one of each other, or to the external device 104.

Figure 2:
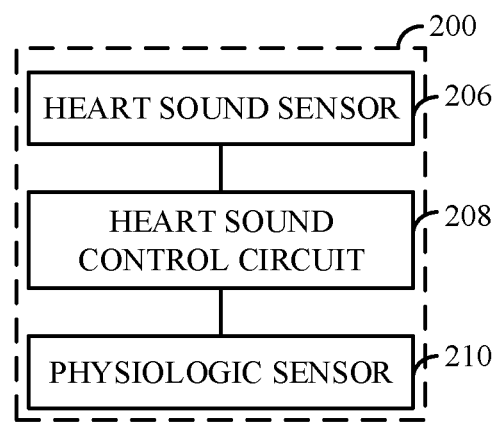

FIG. 2 illustrates an example apparatus 200 including a heart sound sensor 206 and a heart sound control circuit 208. The heart sound sensor 206 can include a sensor, such as an accelerometer, a microphone, a diaphragm, etc., configured to detect or sense heart sound information of the heart, including mechanical or acoustic vibrations resulting from the openings or closures of the valves of the heart, or the movement of blood within, into, or out of the heart, and to produce a heart sound waveform representative of such information.

The heart sound sensor 206 can be configured to detect one or more of a first heart sound (S1), a second heart sound (S2), a third heart sound (S3), or a fourth heart sound (S4) from the heart sound waveform using, for example, one or more respective heart sound windows within one or more physiologic waveform of the patient (e.g., a cardiac waveform, etc.). The heart sound windows can be gated using various physiologic information, for example, electrical information from the heart, one or more other heart sound feature, etc.

In an example, the apparatus 200 can include the insertable cardiac monitor (ICM) 102 from the system 100 illustrated in FIG. 1. In other examples, the apparatus 200 can include one or more other medical devices, including, for example, an implantable medical device (IMD) having one or more leads, with the heart sound sensor 206 positioned on or within a lead coupled to the IMD, or on or within a body of the IMD, or the apparatus 200 can include an insertable or subcutaneous, or external or wearable medical device or patient monitor.

The heart sound sensor 206, or the apparatus 200, can include a plurality of operational modes having different power profiles. An operational mode is one in which the heart sound sensor 206 is actively monitoring the patient, in contrast to, for example, an "off" mode, a calibration mode, or a baseline or an initialization mode where physiologic information may be detected (e.g., in a high or low-power mode), but mainly to establish or correct one or more settings or parameters of the device. For example, the heart sound sensor 206 can include a first, chronic, low-power operational mode, and a second, acute, high-power operational mode. In an example, the second, acute, high-power operational mode can include an existing, low/ultralow-noise, high-resolution operational mode, while the first, chronic, low-power operational mode can be more energy efficient. In other examples, the heart sound sensor 206 can include one or more other higher or lower-power operational modes.

The heart sound control circuit 208 can be configured to control the operational mode of the heart sound sensor using, for example, information from the heart sound sensor 206, or other physiologic information. In certain examples, the apparatus 200 can include a physiologic sensor 210, such as a respiration sensor, an activity sensor, a posture sensor, an electrocardiogram (ECG) sensor, an impedance sensor, etc. Such physiologic sensor 210 can be configured to provide physiologic information from the patient to the heart sound control circuit 208, for example, to gate the heart sound waveform, or to enable control of the operational mode of the heart sound sensor 206 by the heart sound control circuit 208.

Figure 3:
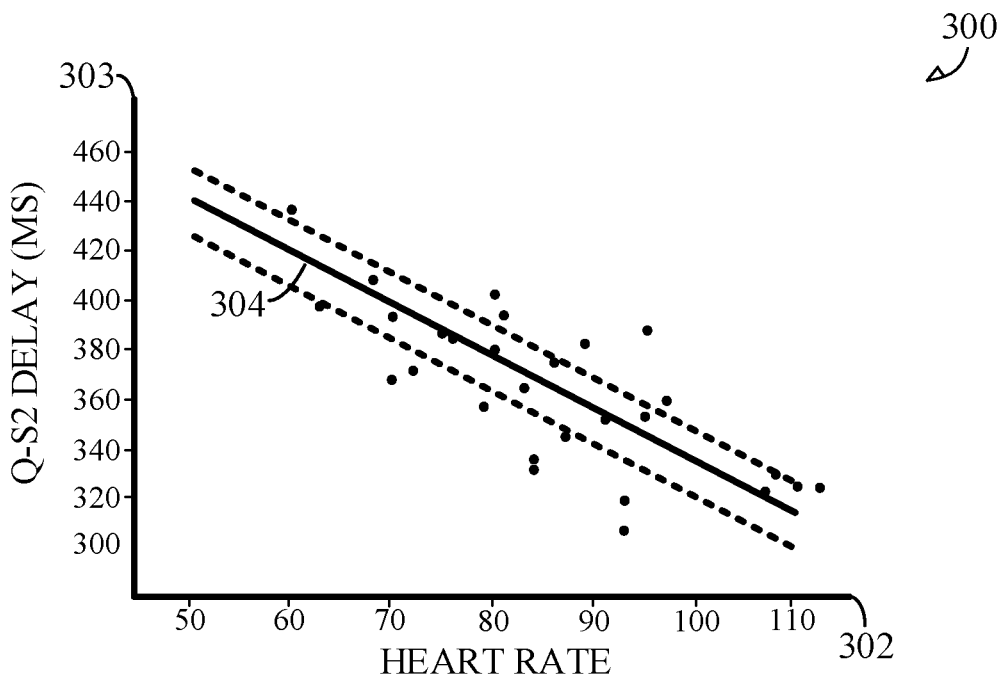
FIG. 3 illustrates an example regression relationship between heart rate (HR) and a Q-S2 delay.

FIG. 3 illustrates an example regression relationship 300 between heart rate (HR) 302 and a Q-S2 delay (ms) 303, including a regression line 304. The present inventors have recognized, among other things, that, as there is a linear relationship between heart rate and the location of S2, the heart rate alone can be used to predict or estimate the location of S2 in a cardiac cycle with respect to the Q-wave or some other physiologic characteristic of the patient, and accordingly, the location of S3 in the cardiac cycle. Thus, S3 can be gated using a detected location of S2 in the heart sound waveform, or by estimating the location of S3 based on heart rate, which can represent significant power savings over detection of the location of the S2. In an example, if using heart rate or one or more other physiologic information to estimate the location of S3, detection of S2 can be periodically made to confirm adequate S3 estimation.

Figure 4:
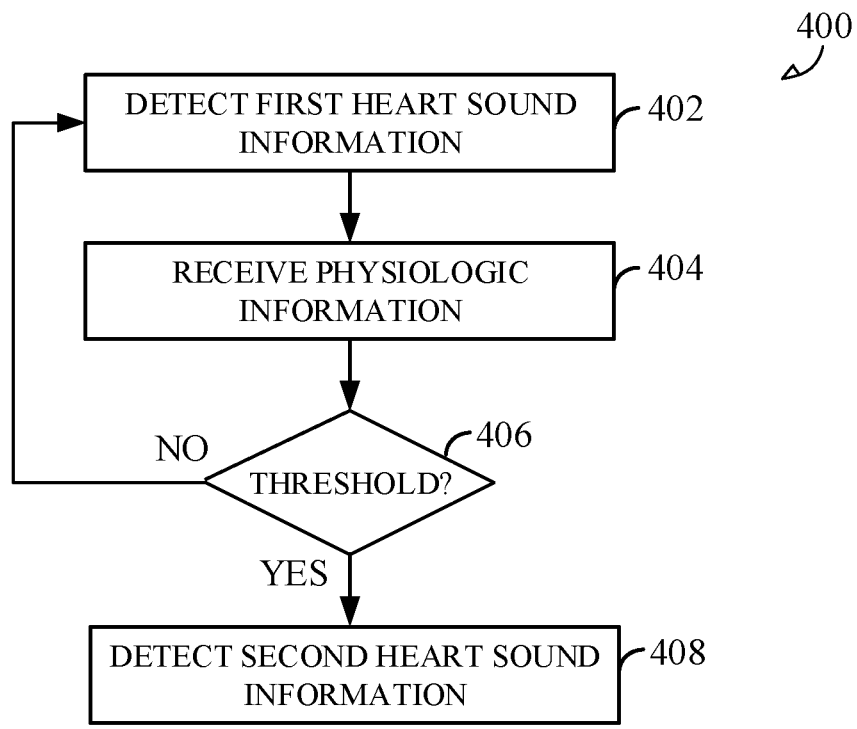
FIG. 4 illustrates an example flow diagram for energy efficient heart sound data collection.

FIG. 4 illustrates a flow diagram for energy efficient heart sound data collection, including detecting heart sound information of a heart of a patient using a heart sound sensor having respective first and second operational modes: a first, low-power operational mode; and a second, high-power operational mode.

At 402, first heart sound information is detected, such as using a heart sound sensor in a first, chronic, low-power operational mode. The low-power operational mode can include a patient-monitoring mode of the heart sound sensor having a lower operating power than at least one other operational patient-monitoring mode of the heart sound sensor.

In certain examples, the low-power operational mode can include a lower sampling frequency, make a fewer number of samples per day, compute a smaller number of (e.g., or shorter) ensemble average sessions per day, have a smaller sampling window for respective heart sounds, record less information in flash memory (e.g., record metrics about a detected heart sound waveform, and not the waveform itself, etc.), store information in non-flash memory for processing, etc. In certain examples, the low-power operational mode can use one or more other physiologic information to determine that low-power operational mode for the heart sound sensor is sufficient (e.g., the low-power heart sound information or one or more other physiologic information indicates that the patient is not experiencing worsening heart failure (HF) or one or more other conditions, such as atrial fibrillation (AF), ischemia, edema, etc.), etc.

At 404, physiologic information is received, such as electrical cardiac information of the patient from an electrocardiogram (ECG) sensor, or one or more other physiologic sensor. In certain examples, the physiologic information can include the first heart sound information detected using the heart sound sensor.

At 406, an indication that the physiologic information exceeds a threshold is determined, for example, using a comparator, etc. In certain examples, the threshold can indicate a worsening status of the patient, a degree of worsening, or an indication that the patient is suffering from one or more condition, including heart failure, etc. In other examples, one or more other triggering conditions can be used. If no, then first heart sound information can be detected at 402. If yes, then process flow proceeds to 408.

At 408, second heart sound information is detected, such as using the heart sound sensor in a second, acute, high-power operational mode. The high-power operational mode can include a patient-monitoring mode of the heart sound sensor having a higher operating power than at least one other operational patient-monitoring mode of the heart sound sensor. In an example, the heart sound sensor can remain in the high-power operational mode for a specific time period, or until the worsening condition resolves.

In certain examples, the high-power operational mode can include a higher sampling frequency, make a greater number of samples per day, compute a larger number of (e.g., or longer) ensemble average sessions per day, have a larger sampling window for respective heart sounds, record more information in flash memory (e.g., record metrics or measurements about a detected heart sound waveform, as well as the waveform itself, etc.), etc. In certain examples, the high-power operational mode can use one or more other physiologic information to determine to stay in the high-power operational mode (e.g., the high-power heart sound information or one or more other physiologic information indicates that the patient is experiencing worsening heart failure (HF) or one or more other conditions, such as atrial fibrillation (AF), ischemia, edema, etc.), etc.

In an example, a certain number of detections of second heart sound information can be made in the second, high-power operational mode, and the remainder of detections can be made in the first, low-power operational mode. For example, if the threshold is exceeded at 406, a first number of detections can be made in the second, high-power operational mode before returning to the first, low-power operational mode for a predetermined time period. In other examples, the threshold at 406 can be increased, etc.

In certain examples, even if the heart sound information or other physiologic information does not exceed a threshold or indicate a worsening patient status or condition, the heart sound sensor can automatically make one or more second heart sound information detections in the second, high-power operational mode at regular intervals (e.g., once or more per day, week, etc.).

Figure 5:
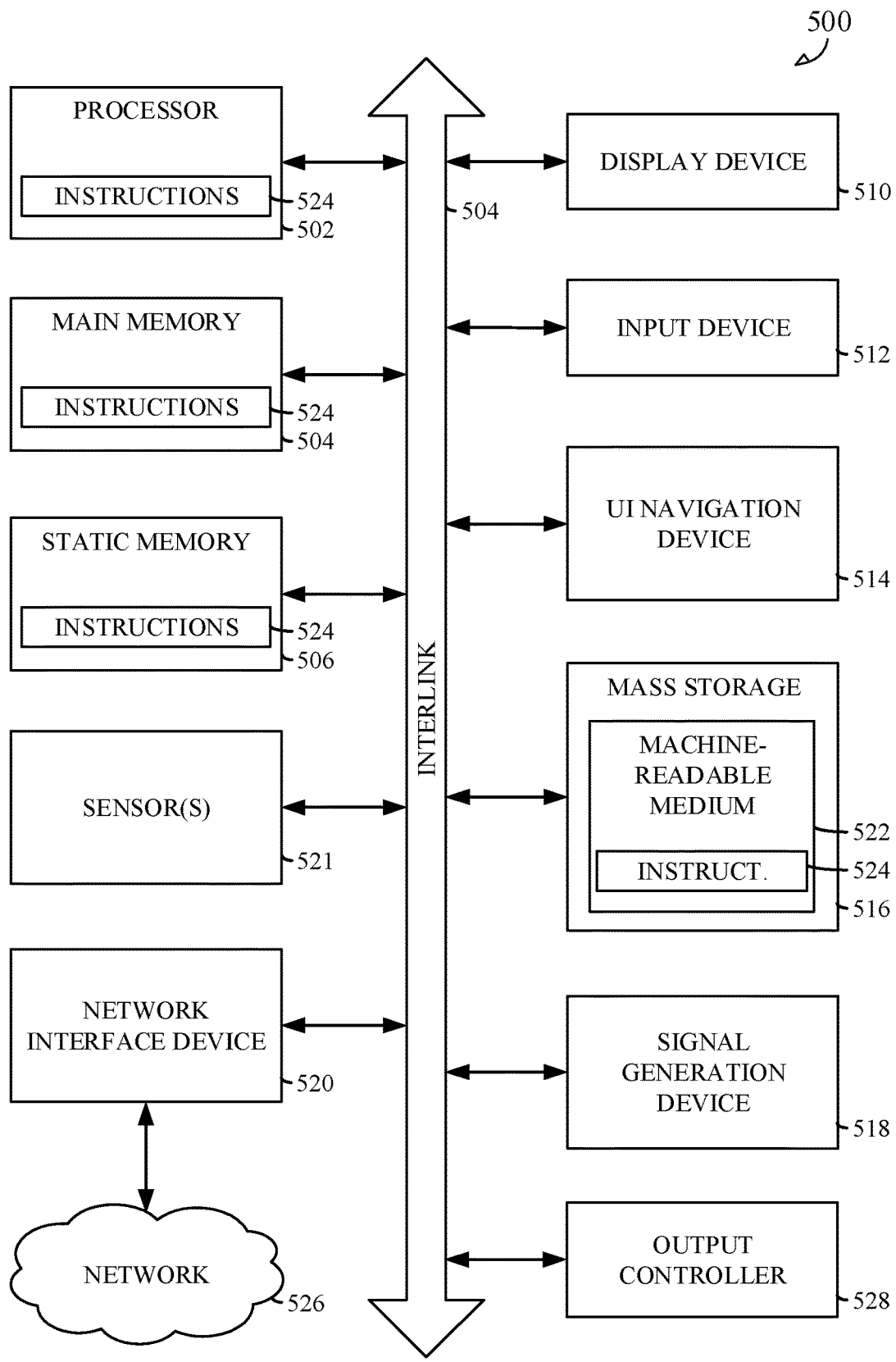
FIG. 5 illustrates an example block diagram of a machine upon which any one or more of the techniques (e.g., methodologies) discussed herein may perform.

FIG. 5 illustrates a block diagram of an example machine 500 upon which any one or more of the techniques (e.g., methodologies) discussed herein may perform. Portions of this description may be applicable to the computing framework of various portions of the LCP device, the IMD, or the external programmer. In alternative embodiments, the machine 500 may operate as a standalone device, a wearable device, or may be connected (e.g., networked) to other machines. In a networked deployment, the machine 500 may operate in the capacity of a server machine, a client machine, or both in server-client network environments. In an example, the machine 500 may act as a peer machine in peer-to-peer (P2P) (or other distributed) network environment. The machine 500 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 500 may include a hardware processor 502 (e.g., a central processing unit (CPU), a graphics processing unit (GPU), a hardware processor core, or any combination thereof), a main memory 504 and a static memory 506, some or all of which may communicate with each other via an interlink (e.g., bus) 508. The machine 500 may further include a display unit 510 (e.g., a raster display, vector display, holographic display, etc.), an alphanumeric input device 512 (e.g., a keyboard), and a user interface (UI) navigation device 514 (e.g., a mouse). In an example, the display unit 510, input device 512 and UI navigation device 514 may be a touch screen display. The machine 500 may additionally include a storage device (e.g., drive unit) 516, a signal generation device 518 (e.g., a speaker), a network interface device 520, and one or more sensors 521, such as a global positioning system (GPS) sensor, compass, accelerometer, or other sensor. The machine 500 may include an output controller 528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 516 may include a machine readable medium 522 on which is stored one or more sets of data structures or instructions 524 (e.g., software) embodying or utilized by any one or more of the techniques or functions described herein. The instructions 524 may also reside, completely or at least partially, within the main memory 504, within static memory 506, or within the hardware processor 502 during execution thereof by the machine 500. In an example, one or any combination of the hardware processor 502, the main memory 504, the static memory 506, or the storage device 516 may constitute machine readable media.

While the machine readable medium 522 is illustrated as a single medium, the term "machine readable medium" may include a single medium or multiple media (e.g., a centralized or distributed database, and/or associated caches and servers) configured to store the one or more instructions 524.

The term "machine readable medium" may include any medium that is capable of storing, encoding, or carrying instructions for execution by the machine 500 and that cause the machine 500 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 524 may further be transmitted or received over a communications network 526 using a transmission medium via the network interface device 520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 520 may include one or more physical jacks (e.g., Ethernet, coaxial, or phone jacks) or one or more antennas to connect to the communications network 526. In an example, the network interface device 520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 500, and includes digital or analog communications signals or other intangible medium to facilitate communication of such software.

Additional Notes

An example (e.g., "Example 1") of matter (e.g., a system) may include a heart sound sensor configured to detect first heart sound information of a heart of a patient in a first, low-power operational mode and to detect second heart sound information of the heart in a separate second, high-power operational mode and a heart sound control circuit configured to receive physiologic information from the patient, and to control the operational mode of the heart sound sensor using the received physiologic information.

In Example 2, the subject matter of Example 1 may optionally be configured such that the heart sound sensor is configured to detect a specified heart sound in a specified heart sound window within at least one physiologic cycle, and the specified heart sound includes at least one of a first heart sound (S1), a second heart sound (S2), a third heart sound (S3), or a fourth heart sound (S4), and the specified heart sound window includes at least one of a first, second, third, or fourth heart sound window corresponding to the specified heart sound.

In Example 3, the subject matter of any one or more of Examples 1-2 may optionally be configured such that the first and second heart sound information includes an ensemble average of a specified heart sound in a specified heart sound window over more than one physiologic cycle.

In Example 4, the subject matter of any one or more of Examples 1-3 may optionally be configured such that the ensemble average is determined at a rate of a first number per day in the first mode, and at a rate of a second, higher number per day in the second mode, or the ensemble average is determined over a first period in the first mode, and over a second, longer period in the second mode.

In Example 5, the subject matter of any one or more of Examples 1-4 may optionally be configured such that the control circuit is configured to receive heart sound information from the heart sound sensor, and to control the operational mode of the heart sound sensor using the received heart sound information, and the heart sound control circuit is configured to transition the heart sound sensor from the first mode to the second mode when the first heart sound information exceeds a threshold.

In Example 6, the subject matter of any one or more of Examples 1-5 may optionally be configured such that the heart sound control circuit is configured to transition the heart sound sensor from the first mode to the second mode when the received physiologic information from the patient indicates worsening heart failure.

In Example 7, the subject matter of any one or more of Examples 1-6 may optionally be configured such that the heart sound sensor has a first sampling frequency in the first mode and a second, higher sampling frequency in the second mode.

In Example 8, the subject matter of any one or more of Examples 1-7 may optionally be configured such that the heart sound sensor is configured to detect the first heart sound information in the first mode using a first specified heart sound window having a first duration within at least one physiologic cycle, and the heart sound sensor is configured to detect the second heart sound information in the second mode using a second specified heart sound window having a second duration longer than the first duration within at least one physiologic cycle.

In Example 9, the subject matter of any one or more of Examples 1-8 may optionally be configured such that the heart sound control circuit is configured, in the first mode, to determine a location of the first specified heart sound window in a physiologic cycle using the received physiologic information, and, in the second mode, to determine a location of the second specified heart sound window in a physiologic cycle using a detected timing of at least one other heart sound in the physiologic cycle.

In Example 10, the subject matter of any one or more of Examples 1-9 may optionally be configured such that the first and second heart sound information includes third heart sound (S3) information, the physiologic information includes heart rate information from the patient, and the heart sound control circuit is configured, in the second mode, to determine the location of the second specified heart sound window in a physiologic cycle using a detected timing of a second heart sound (S2) in the physiologic cycle.

An example (e.g., "Example 11") of matter (e.g., a method) may include detecting first heart sound information of a heart of a patient using a heart sound sensor in a first, low-power operational mode, detecting second heart sound information of the heart using the heart sound sensor in a separate second, high-power operational mode, receiving, using a heart sound control circuit, physiologic information from the patient and controlling the operational mode of the heart sound sensor using the received physiologic information.

In Example 12, the subject matter of Example 11 may optionally include determining, in the first mode, an ensemble average of a specified heart sound in a specified heart sound window over more than one physiologic cycle using the first heart sound information, and determining, in the second mode, an ensemble average of a specified heart sound in a specified heart sound window over more than one physiologic cycle using the second heart sound information, wherein determining the ensemble average includes at a rate of a first number per day in the first mode, each having a first period, and at a rate of a second, higher number per day in the second mode, each having a second, longer period.

In Example 13, the subject matter of any one or more of Examples 11-12 may optionally be configured such that detecting the first heart sound information in the first mode includes using a first sampling frequency and a first specified heart sound window having a first duration, and detecting the second heart sound information in the second mode includes using a second sampling frequency higher than the first sampling frequency and a second specified heart sound window having a second duration longer than the first duration.

In Example 14, the subject matter of any one or more of Examples 11-13 may optionally be configured such that determining a location of the first specified heart sound window in a physiologic cycle using the received physiologic information, and determining a location of the second specified heart sound window in a physiologic cycle using a detected timing of at least one other heart sound in the physiologic cycle.

In Example 15, the subject matter of any one or more of Examples 11-14 may optionally be configured such that the heart sound control circuit is configured to transition the heart sound sensor from the first mode to the second mode when the received physiologic information from the patient indicates worsening heart failure.

An example (e.g., "Example 16") of matter (e.g., a system) may include a heart sound sensor configured to detect first heart sound information of a heart of a patient in a first, low-power operational mode and to detect second heart sound information of the heart in a separate second, high-power operational mode, and a heart sound control circuit configured to receive physiologic information from the patient, and to control the operational mode of the heart sound sensor using the received physiologic information.

In Example 17, the subject matter of Example 16 may optionally be configured such that the heart sound sensor has a first sampling frequency in the first mode and a second, higher sampling frequency in the second mode.

In Example 18, the subject matter of any one or more of Examples 16-17 may optionally be configured such that the heart sound sensor is configured to detect the first heart sound information in the first mode using a first specified heart sound window having a first duration within at least one physiologic cycle, and the heart sound sensor is configured to detect the second heart sound information in the second mode using a second specified heart sound window having a second duration longer than the first duration within at least one physiologic cycle.

In Example 19, the subject matter of any one or more of Examples 16-18 may optionally be configured such that the heart sound control circuit is configured, in the first mode, to determine a location of the first specified heart sound window in a physiologic cycle using the received physiologic information, and, in the second mode, to determine a location of the second specified heart sound window in a physiologic cycle using a detected timing of at least one other heart sound in the physiologic cycle.

In Example 20, the subject matter of any one or more of Examples 16-19 may optionally be configured such that the first and second heart sound information includes third heart sound (S3) information, the physiologic information includes heart rate information from the patient, and the heart sound control circuit is configured, in the second mode, to determine the location of the second specified heart sound window in a physiologic cycle using a detected timing of a second heart sound (S2) in the physiologic cycle.

In Example 21, the subject matter of any one or more of Examples 16-20 may optionally be configured such that the heart sound sensor is configured to detect a specified heart sound in a specified heart sound window within at least one physiologic cycle, and the specified heart sound includes at least one of a first heart sound (S1), a second heart sound (S2), a third heart sound (S3), or a fourth heart sound (S4), and the specified heart sound window includes at least one of a first, second, third, or fourth heart sound window corresponding to the specified heart sound.

In Example 22, the subject matter of any one or more of Examples 16-21 may optionally be configured such that the first and second heart sound information includes an ensemble average of a specified heart sound in a specified heart sound window over more than one physiologic cycle.

In Example 23, the subject matter of any one or more of Examples 16-22 may optionally be configured such that the ensemble average is determined at a rate of a first number per day in the first mode, and at a rate of a second, higher number per day in the second mode, or the ensemble average is determined over a first period in the first mode, and over a second, longer period in the second mode.

In Example 24, the subject matter of any one or more of Examples 16-23 may optionally be configured such that the control circuit is configured to receive heart sound information from the heart sound sensor, and to control the operational mode of the heart sound sensor using the received heart sound information, and the heart sound control circuit is configured to transition the heart sound sensor from the first mode to the second mode when the first heart sound information exceeds a threshold.

In Example 25, the subject matter of any one or more of Examples 16-24 may optionally be configured such that the heart sound control circuit is configured to transition the heart sound sensor from the first mode to the second mode when the received physiologic information from the patient indicates worsening heart failure.

An example (e.g., "Example 26") of matter (e.g., a method) may include detecting first heart sound information of a heart of a patient using a heart sound sensor in a first, low-power operational mode, detecting second heart sound information of the heart using the heart sound sensor in a separate second, high-power operational mode, and receiving, using a heart sound control circuit, physiologic information from the patient and controlling the operational mode of the heart sound sensor using the received physiologic information.

In Example 27, the subject matter of Example 26 may optionally be configured such that detecting the first heart sound information in the first mode includes using a first sampling frequency, and detecting the second heart sound information in the second mode includes using a second sampling frequency higher than the first sampling frequency.

In Example 28, the subject matter of any one or more of Examples 26-27 may optionally be configured such that detecting the first heart sound information in the first mode includes using a first specified heart sound window having a first duration within at least one physiologic cycle, and detecting the second heart sound information in the second mode includes using a second specified heart sound window having a second duration longer than the first duration within at least one physiologic cycle.

In Example 29, the subject matter of any one or more of Examples 26-28 may optionally include determining a location of the first specified heart sound window in a physiologic cycle using the received physiologic information, and determining a location of the second specified heart sound window in a physiologic cycle using a detected timing of at least one other heart sound in the physiologic cycle.

In Example 30, the subject matter of any one or more of Examples 26-29 may optionally be configured such that detecting the first and second heart sound information includes detecting third heart sound (S3) information, receiving physiologic information includes receiving heart rate information from the patient in the first mode, and determining the location of the second specified heart sound window includes using a detected timing of a second heart sound (S2) in the physiologic cycle.

In Example 31, the subject matter of any one or more of Examples 26-30 may optionally be configured such that detecting the first and second heart sound information includes detecting a specified heart sound in a specified heart sound window within at least one physiologic cycle, and the specified heart sound includes at least one of a first heart sound (S1), a second heart sound (S2), a third heart sound (S3), or a fourth heart sound (S4), and the specified heart sound window includes at least one of a first, second, third, or fourth heart sound window corresponding to the specified heart sound.

In Example 32, the subject matter of any one or more of Examples 26-31 may optionally include determining, in the first mode, an ensemble average of a specified heart sound in a specified heart sound window over more than one physiologic cycle using the first heart sound information, and determining, in the second mode, an ensemble average of a specified heart sound in a specified heart sound window over more than one physiologic cycle using the second heart sound information.

In Example 33, the subject matter of any one or more of Examples 26-33 may optionally be configured such that determining the ensemble average includes at a rate of a first number per day in the first mode, and at a rate of a second, higher number per day in the second mode, or determining the ensemble average includes over a first period in the first mode, and over a second, longer period in the second mode.

In Example 34, the subject matter of any one or more of Examples 26-33 may optionally be configured such that the control circuit is configured to receive heart sound information from the heart sound sensor, and to control the operational mode of the heart sound sensor using the received heart sound information, and the heart sound control circuit is configured to transition the heart sound sensor from the first mode to the second mode when the first heart sound information exceeds a threshold.

In Example 35, the subject matter of any one or more of Examples 26-341-2 may optionally be configured such that the heart sound control circuit is configured to transition the heart sound sensor from the first mode to the second mode when the received physiologic information from the patient indicates worsening heart failure.

An example (e.g., "Example 36") of subject matter (e.g., a system or apparatus) may optionally combine any portion or combination of any portion of any one or more of Examples 1-35 to include "means for" performing any portion of any one or more of the functions or methods of Examples 1-35, or a "machine-readable medium" (e.g., massed, non-transitory, etc.) including instructions that, when performed by a machine, cause the machine to perform any portion of any one or more of the functions or methods of Examples 1-35.

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
   a heart sound sensor configured to detect first heart sound information of a heart of a patient in a first, low-power operational mode and to detect second heart sound information of the heart in a separate second, high-power operational mode, wherein the heart sound sensor is more energy efficient in the first, low-power operational mode than in the second, high-power operational mode; and
   a heart sound control circuit configured to receive physiologic information from the patient, and to control the operational mode of the heart sound sensor using the received physiologic information, wherein the operational mode of the heart sound sensor includes the first, low-power operational mode and the second, high-power operational mode.

2. The system of claim 1, wherein the heart sound sensor has a first sampling frequency in the first mode and a second, higher sampling frequency in the second mode.

3. The system of claim 1, wherein the heart sound sensor is configured to detect the first heart sound information in the first mode using a first specified heart sound window having a first duration within at least one physiologic cycle, and
   wherein the heart sound sensor is configured to detect the second heart sound information in the second mode using a second specified heart sound window having a second duration longer than the first duration within at least one physiologic cycle.

4. The system of claim 3, wherein the heart sound control circuit is configured, in the first mode, to determine a location of the first specified heart sound window in a physiologic cycle using the received physiologic information, and, in the second mode, to determine a location of the second specified heart sound window in a physiologic cycle using a detected timing of at least one other heart sound in the physiologic cycle.

5. The system of claim 4, wherein the first and second heart sound information includes third heart sound (S3) information,
   wherein the physiologic information includes heart rate information from the patient, and
   wherein the heart sound control circuit is configured, in the second mode, to determine the location of the second specified heart sound window in a physiologic cycle using a detected timing of a second heart sound (S2) in the physiologic cycle.

6. The system of claim 1, wherein the heart sound sensor is configured to detect a specified heart sound in a specified heart sound window within at least one physiologic cycle, and
   wherein the specified heart sound includes at least one of a first heart sound (S1), a second heart sound (S2), a third heart sound (S3), or a fourth heart sound (S4), and the specified heart sound window includes at least one of a first, second, third, or fourth heart sound window corresponding to the specified heart sound.

7. The system of claim 1, wherein the first and second heart sound information includes an ensemble average of a specified heart sound in a specified heart sound window over more than one physiologic cycle.

8. The system of claim 7, wherein the ensemble average is determined at a rate of a first number per day in the first mode, and at a rate of a second, higher number per day in the second mode, or
wherein the ensemble average is determined over a first period in the first mode, and over a second, longer period in the second mode.

9. The system of claim 1, wherein the control circuit is configured to receive heart sound information from the heart sound sensor, and to control the operational mode of the heart sound sensor using the received heart sound information, and
wherein the heart sound control circuit is configured to transition the heart sound sensor from the first mode to the second mode when the first heart sound information exceeds a threshold.

10. The system of claim 1, wherein the heart sound control circuit is configured to transition the heart sound sensor from the first mode to the second mode when the received physiologic information from the patient indicates worsening heart failure.

11. A method, comprising:
detecting first heart sound information of a heart of a patient using a heart sound sensor in a first, low-power operational mode;
detecting second heart sound information of the heart using the heart sound sensor in a separate second, high-power operational mode, wherein the first, low-power operational mode is more energy efficient than the second, high-power operational mode; and
receiving, using a heart sound control circuit, physiologic information from the patient and controlling the operational mode of the heart sound sensor using the received physiologic information, wherein the operational mode of the heart sound sensor includes the first, low-power operational mode and the second, high-power operational mode.

12. The method of claim 11, wherein detecting the first heart sound information in the first mode includes using a first sampling frequency, and
wherein detecting the second heart sound information in the second mode includes using a second sampling frequency higher than the first sampling frequency.

13. The method of claim 11, wherein detecting the first heart sound information in the first mode includes using a first specified heart sound window having a first duration within at least one physiologic cycle, and
wherein detecting the second heart sound information in the second mode includes using a second specified heart sound window having a second duration longer than the first duration within at least one physiologic cycle.

14. The method of claim 13, including:
determining a location of the first specified heart sound window in a physiologic cycle using the received physiologic information; and
determining a location of the second specified heart sound window in a physiologic cycle using a detected timing of at least one other heart sound in the physiologic cycle.

15. The method of claim 14, wherein detecting the first and second heart sound information includes detecting third heart sound (S3) information,
wherein receiving physiologic information includes receiving heart rate information from the patient in the first mode, and
wherein determining the location of the second specified heart sound window includes using a detected timing of a second heart sound (S2) in the physiologic cycle.

16. The method of claim 11, wherein detecting the first and second heart sound information includes detecting a specified heart sound in a specified heart sound window within at least one physiologic cycle, and
wherein the specified heart sound includes at least one of a first heart sound (S1), a second heart sound (S2), a third heart sound (S3), or a fourth heart sound (S4), and the specified heart sound window includes at least one of a first, second, third, or fourth heart sound window corresponding to the specified heart sound.

17. The method of claim 11, including:
determining, in the first mode, an ensemble average of a specified heart sound in a specified heart sound window over more than one physiologic cycle using the first heart sound information; and
determining, in the second mode, an ensemble average of a specified heart sound in a specified heart sound window over more than one physiologic cycle using the second heart sound information.

18. The method of claim 17, wherein determining the ensemble average includes at a rate of a first number per day in the first mode, and at a rate of a second, higher number per day in the second mode, or
wherein determining the ensemble average includes over a first period in the first mode, and over a second, longer period in the second mode.

19. The method of claim 11, wherein the control circuit is configured to receive heart sound information from the heart sound sensor, and to control the operational mode of the heart sound sensor using the received heart sound information, and
wherein the heart sound control circuit is configured to transition the heart sound sensor from the first mode to the second mode when the first heart sound information exceeds a threshold.

20. The method of claim 11, wherein the heart sound control circuit is configured to transition the heart sound sensor from the first mode to the second mode when the received physiologic information from the patient indicates worsening heart failure.

* * * * *